United States Patent [19]
Baszczynski et al.

[11] Patent Number: 5,401,836
[45] Date of Patent: Mar. 28, 1995

[54] BRASSICA REGULATORY SEQUENCE FOR ROOT-SPECIFIC OR ROOT-ABUNDANT GENE EXPRESSION

[75] Inventors: Chris L. Baszczynski, Acton; Lynne Fallis, Caledon East; Guy Bellemare, Sillery; Rodolphe Boivin, Quebec, all of Canada

[73] Assignee: Pioneer Hi-Bre International, Inc., Des Moines, Iowa

[21] Appl. No.: 915,246

[22] Filed: Jul. 16, 1992

[51] Int. Cl.6 .................. C07H 17/00; C07H 21/04; C12N 15/00
[52] U.S. Cl. .................. 536/24.1; 536/23.1; 435/172.3; 435/320.1; 935/35; 935/6
[58] Field of Search .............. 536/27, 23.1, 24.1; 435/172.1, 172.3, 320.1; 935/6, 33, 35, 64, 67

[56] References Cited

U.S. PATENT DOCUMENTS

| | | | |
|---|---|---|---|
| 4,803,165 | 2/1989 | Applebaum | 435/172.3 |
| 4,943,674 | 7/1990 | Houck et al. | 800/205 |
| 5,008,194 | 4/1991 | Rolfe et al. | 435/172.3 |
| 5,023,079 | 6/1991 | Lam et al. | 435/172.3 |

FOREIGN PATENT DOCUMENTS 9007001  6/1990  WIPO ................... C12N 15/56

OTHER PUBLICATIONS

K J Brunke et al (1991) Tibtech 9:197-200.
Matzke, et al., "Deletion Analysis of a Zein Gene Promoter in Transgenic Tobacco Plants," Plant Molecular Biology 14:323-332 (1990).
Hamilton et al., "Dissection of a Pollen-Specific Promoter from Maize by Transient Transformation Assays," 18 211-218 (1992).
Ellis, et al., "Tissue-Specific Expression of a Pea Legumin Gene in Seeds of Nicotiana plumbaginifolia," Plant Molecular Biology, 10 203-214 (1988).
Arnoldo, et al., "Functional Analysis of Heterologous Anther/Pollen-Specific Promoters in Transgenic Brassica Napus," J. of Cellular Biochemistry, Abstract No. Y 101, p. 204 Apr. 3-16, 1992.
B S de Pater et al (1992) Plant Molecular Biology 18:161-164.
Y T Yamamoto et al (1991) Plant Cell 3:371-382.
T Hoff et al (1991) Physiologia Plantarum 82:197-204.
T L Noland et al (1990) Plant Physiology 93(1 Sup):145.
Baszczynski, Chris L., "Gene Expression From Brassica Napus tissue-Specific Promoters in Transgenic Plants,"0 Poster Abstract, at the International society for Plant Molecular Biology Third International Congress, was presented in Oct., 1991.
Guerrero et al., "Promoter Sequences From A Maize Pollen-Specific Gene Directed tissue-Specific Transscription In Tobacco," Mol. Gen. Genet. (1990) 244: 161-168.
Ohl, et al., "Functional Properties Of A Phenylalanine Ammonia-Lyase Promoter from Arabidopsis," The Plant Cell, vol. 2, 837-849 Sep. 1990.
Van der Meer, et al., "Promoter Analysis of the Cha-lene Synthase (chsA) Gene of Petunia hybrida: A 67 bp (List continued on next page.)

Primary Examiner—David T. Fox
Assistant Examiner—Bruce Campell
Attorney, Agent, or Firm—Foley & Lardner

[57] ABSTRACT

The present invention is directed to an isolated promoter element that exhibits root abundant expression in Brassica sp. The promoter element has particular utility in driving the transcription of heterologous structural proteins that confer disease immunity or resistance to disease susceptible roots. The word "disease" encompasses any adverse condition caused to a plant by an organism other than itself, such as fungi, bacteria, and insects. Plasmids incorporating the promoter are disclosed.

9 Claims, 13 Drawing Sheets

```
     -518
       |
       TATGGCTTA TTATACTGAT GCCCCGATTC CACTAAAATA
-479 CTCTAATCTC TAGATGTAGA ATTTGAGTGC TTTCTAAATT GAAAGAATTT
-429 GTAAATGAAC GATCAACCAA AATAAATAAT GATGAAAATG TATATTGTCA
-379 CAATTGATAA ACAATACTAT TTTCTGTATG AAACGTCTTA AAACAAACAT
-329 TTCACTTTTA TGTTTTCCAG TTTAGATTTT ACTCCGTCAT TTATATCTTA
-279 AATTATTGGT GTTCTACCAT ATGATTAATT ATATACTTCA AAGCCGGCAT
-229 ACATGGAAGA TTTTTTTTAT AATGACACTA CAACATGCAT CAAAGCAACA
-179 AAAATCATAG ATACACTGGA TGGAATTGAT AGGTGAGGTT TGGGCCCCAA
-129 CAACTGAGCA TTAGACATCT TATCCTATGT GCAACCAACG CGGTTAGGTC
 -79 TGGTGAAATG CCTATAAATA CGGACACATT CTCAAGCAAA CTCATCACAC
 -29 AACAAAATCG TAAGAAGAAA GAGTGAAAC
                                         |
                                        -1
```

OTHER PUBLICATIONS

Promoter Region Directs Flower-Specific Expression," Plant Molecular Biol., 15:95-109, 1990.

Vorst, et al., "Tissue-Specific Expression Directed By an Arabidopsis thaliana Preferredoxin Promoter In Transgenic Tobacco Plants," Plant Molecular Biology, 14: 491-499 1990.

Tingey, et al., "Glutamine Synthetase Genes Of PCA Encode Distinct Polypeptides Which Are Differentially Expressed In Leaves, Roots And Nodules," EMBO J., 6:1 1-9 1987.

Takaiwa, et al., "Analysis Of The 5' Flanking Region Responsible for the Endosperm-Specific Expression of a Rice Glutelin Chimeric Gene in Transgenic Tobacco," Plant Mol. Biol., 16: 49-58, 1991.

Vander Zaal et al., "Promoters of Auxin-induced Genes From Tobacco Can Lead to Auxin-inducible and Root Tip-Specific Expression," Plant Mol. Biol., 16:983-998 1991.

Oppenheimer et al., "The B-Tubulin Gene Family of Arabidgasis thaliana: Preferential Accumulation of the B1 Transcript in Roots", Gene, 63 (1988) 87-102.

Conkling et al., "Isolation of Transcriptionally Regulated Root-Specific Genes from Tobacco," Plant Physiol., 93 (1990) 1203-1211.

Bellemare et al., "Use of a Phage Vector for Rapid Synthesis and Cloning of Single Stranded cDNA," Gene, 52 (1987). 11-19.

Wong et al., "Transcriptional and Translational Start Sites for the *Bacillus thuringiensis* Crystal Protein Gene," J. Biol. Chem., 258 (1983) 1960 1967.

Kamalay, et al., "Organ-specific Nuclear RNAs in Tobacco," Proc. Natl. Acad. Sci USA, 81:(1984) 2801-2805.

FIG. 4A

```
-551  ATTCATTGAT GATCGACAAA ATATGTTATT ATATATGGCT TATTATACTG
-501  ATGCCCCGAT TCCACTAAAA TACTCTAATC TCTAGATGTA GAATTTGAGT
-451  GCTTTCTAAA TTGAAAGAAT TTGTAAATGA ACGATCAACC AAAATAAATA
-401  ATGATGAAAA TGTATATTGT CACAATTGAT AAACAATACT ATTTTCTGTA
-351  TGAAACGTCT TAAAACAAAC ATTTCACTTT TATGTTTTCC AGTTTAGATT
-301  TTACTCCGTC ATTTATATCT TAAATTATTG GTGTTCTACC ATATGATTAA
-251  TTATATACTT CAAAGCCGGC ATACATGGAA GATTTTTTTT ATAATGACAC
-201  TACAACATGC ATCAAAGCAA CAAAAATCAT AGATACACTG GATGGAATTG
-151  ATAGGTGAGG TTTGGGCCCC AACAACTGAG CATTAGACAT CTTATCCTAT
-101  GTGCAACCAA CGCGGTTAGG TCTGGTGAAA TGCCTATAAA TACGGACACA
                                   ↓
 -51  TTCTCAAGCA AACTCATCAC ACAACAAAAT CGTAAGAAGA AAGAGTGAAA
  -1  CATGGCTAAT CACAAAAATC TTTTCTTCCT ATGTTTCTTA ATAGGTTTAG
  50  GGTTATGTTC TGCAAGACGA GCACTTCTTT CCTCCTATGA ACCCGAGGAT
 100  GAAGTCGCCG GATACGGCGA GAAAGTAGT TTGCATGCTG GTTATGGTAT
 150  TGGAGTTGAT GCTGGTGTTG GTGTTGGAGG TGGTGGCGGA GAAGGAGGTG
 200  GTGCTGGTTA CGGTGGAGCT GAAGGCATTG GTGGAGGAGG AGGCGGTGGA
 250  CATGGTGGTG GTGCTGGTGG AGGTGGTGGT GGTGGTCCTG GAGGAGGATC
 300  TGGTTATGGA GGTGGAAGCG GTGAAGGTGG TGGAGCTGGA TACGGAGGCG
 350  GAGGAGCTGG AGGACATGGT GGAGGTGGAG GAAGCGGAGG AGGTGGTGGT
 400  GGAGGAGCTG GCGGTGCGCA TGGTGGTGGA TACGGTGGTG GAGAAGGTGC
 450  TGGTGCTGGA GGAGGATATG GAGGTGGCGG TGCAGGTGGA CATGGAGGTG
 500  GTGGAGGCGG TGGAAATGGA GGCGGTGGAG GAGGTGGAGG TGCACACGGT
 550  GGTGGATACG GTGGTGGAGA AGGCGCTGGT GCTGGAGGAG GATATGGAGG
 600  TGGCGGTGCA GGTGGACATG GAGGTGGTGG AGGCGGGGGA AAAGGAGGCG
```

FIG. 4B

```
650  GTGGAGGAGG AGGTTCTGGC GCCGGTGGAG CTCACGGTGG TGGTTATGGT
700  GCCGGAGGTG GAGCTGGAGA GGGATACGGT GGTGGTGGTG GAGAAGGAGG
750  ACACGGTGGT GGAGGAGGCG GTGGTGGTGG AGCTGGAGGT GGCGGAGGAG
800  GAGGGGGAGG TTATGCAGCT GCTGGATCAG GACACGGTGG CGGTGCTGGT
850  AGGGGAGAAG GTGGTGGTGG CTATTAACAC CGTGAAATTA TCTATGTGGA
900  GCGTAAGGGC CATTGAGTAA AGTGTCATAT AACTGGTAAG AGACTATATT
950  TACAC
```

FIG. 6

```
      -518
       |
       GGGTTAAGCT TTATGGCTTA TTATACTGAT GCCCCGATTC CACTAAAATA
            HindIII

-479   CTCTAATCTC TAGATGTAGA ATTTGAGTGC TTTCTAAATT GAAAGAATTT

-429   GTAAATGAAC GATCAACCAA AATAAATAAT GATGAAAATG TATATTGTCA

-379   CAATTGATAA ACAATACTAT TTTCTGTATG AAACGTCTTA AAACAAACAT

-329   TTCACTTTTA TGTTTTCCAG TTTAGATTTT ACTCCGTCAT TTATATCTTA

-279   AATTATTGGT GTTCTACCAT ATGATTAATT ATATACTTCA AAGCCGGCAT

-229   ACATGGAAGA TTTTTTTTAT AATGACACTA CAACATGCAT CAAAGCAACA

-179   AAAATCATAG ATACACTGGA TGGAATTGAT AGGTGAGGTT TGGGCCCCAA

-129   CAACTGAGCA TTAGACATCT TATCCTATGT GCAACCAACG CGGTTAGGTC

-79    TGGTGAAATG CCTATAAATA CGGACACATT CTCAAGCAAA CTCATCACAC

-29    AACAAAATCG TAAGAAGAAA GAGTGAAACT CTAGAAACCC
                                         XbaI
                                          |
                                         -1
```

FIG. 7

```
       TATGGCTTA TTATACTGAT GCCCCGATTC CACTAAAATA
-518
-479   CTCTAATCTC TAGATGTAGA ATTTGAGTGC TTTCTAAATT GAAAGAATTT
-429   GTAAATGAAC GATCAACCAA AATAAATAAT GATGAAAATG TATATTGTCA
-379   CAATTGATAA ACAATACTAT TTTCTGTATG AAACGTCTTA AAACAAACAT
-329   TTCACTTTTA TGTTTTCCAG TTTAGATTTT ACTCCGTCAT TTATATCTTA
-279   AATTATTGGT GTTCTACCAT ATGATTAATT ATATACTTCA AAGCCGGCAT
-229   ACATGGAAGA TTTTTTTTAT AATGACACTA CAACATGCAT CAAAGCAACA
-179   AAAATCATAG ATACACTGGA TGGAATTGAT AGGTGAGGTT TGGGCCCCAA
-129   CAACTGAGCA TTAGACATCT TATCCTATGT GCAACCAACG CGGTTAGGTC
-79    TGGTGAAATG CCTATAAATA CGGACACATT CTCAAGCAAA CTCATCACAC
-29    AACAAAATCG TAAGAAGAAA GAGTGAAAC
                                    -1
```

BRASSICA REGULATORY SEQUENCE FOR ROOT-SPECIFIC OR ROOT-ABUNDANT GENE EXPRESSION

FIELD OF THE INVENTION

The present invention is directed to an isolated promoter for root abundant gene expression. More particularly, the present invention is also directed to a composite gene comprising the isolated promoter in combination with a heterologous structural gene, preferably a heterologous gene encoding a protein or peptide that when expressed in the roots of a plant confers immunity or resistance to disease to the roots of the plant. The present invention is useful because it provides a promoter and a method for genetically conferring immunity or resistance to disease to the roots of transformable plants.

BACKGROUND OF THE INVENTION

In canola as well as other crops, various fungal and insect diseases exist that are manifested in the roots of the plant. Although the plant's roots are underground, conventional methods of treatment to prevent or control root diseases come from above ground. These conventional treatments include the application of a variety of chemicals via sprays, granules and the like. These conventional treatments are both labor intensive and costly. Often, the exposed edible portion of the crop plant receives application of the chemical agent that is intended for localization at the roots. On occasion, the conventional treatments require that the applied chemical agent be worked into the ground. However, care must be exercised to avoid damaging the plant's roots. Because conventional treatments are applied from above ground, excess quantities of the chemical agent must be applied to maintain an effective concentration at the portion of the root zone furthest from the application point.

It is an object of the present invention to provide a means for generally or specifically conferring immunity or resistance to fungal or insect diseases on a plant whose roots are susceptible to such a disease.

It is a further object of the present invention to provide the components and a method for conferring disease resistance on the roots of food crops that eliminates conventional treatments and that exhibits minimal or no manifestation in the edible fruit or leafy portions of the plant.

The process of tissue and organ development in plants involves the temporal and spatial expression of a large array of genes that determine the patterns of cell division, elongation and differentiation leading to the final structure and function of the tissue or organ. For example, Kamalay and Goldberg (Cell 19:935, 1980; Proc. Natl. Acad. Sci. USA, 81:2801, 1984) estimated that as many as 25,000 diverse genes may be expressed in the tobacco anther. Of these, as many as 10,000 are anther-specific. While these many genes may not be unique to every organ, many tissue types from several species have been studied to date, and have revealed sets of genes which appear to be either uniquely, or predominantly expressed in individual tissues.

The identification and isolation of genes associated with tissue-specific expression in *Brassica* species has been less prevalent, but several genes exhibiting tissue- or stage-dependent expression have been isolated and characterized. These include genes unique to or abundant in seed (Simon et al., Plant Mol. Biol. 5:191, 1985; Scofield and Crouch, J. Biol. Chem. 262:12202, 1987; Baszczynski and Fallis, Plant Mol. Biol. 14:633, 1990); leaf (Baszczynski et al., Nuc. Acids Res. 16:4732, 1988; Boivin et al., in preparation); stigma (Nasrallah et al., Proc. Natl. Acad. Sci. USA 85:5551, 1988; Trick, Plant Mol. Biol. 15:203, 1990), microspore and pollen (Albani et al., Plant Mol. Biol. 15:605, 1990; Albani et al., Plant Mol. Biol. 16:501, 1991); and recently, root (Fallis and Baszczynski unpublished; Bergeron et al., in preparation). In the last several years, promoters have been fused to reporter or other agronomic genes for molecular transformation, and the degree and specificity of expression has been measured. Examples include Stockhaus et al. (Proc. Natl. Acad. Sci. USA 85:7943, 1987); An et al. (Plant Physiol. 88:547, 1988); Ellis et al. (Plant Mol. Biol. 10:203, 1988); Guerrero et al. (Mol. Gen. Genet. 224:161, 1990); Ohl et al. (Cell 2:837, 1990); van der Meer et al. (Plant Mol. Biol. 15:95, 1990); Vorst et al. (Plant Mol. Biol. 14:491, 1990); Baszczynski et al. (Proc. 3rd ISPMB Internat. Congr., Tucson, Arizona, abstr. 430, 1991); Takaiwa et al. (Plant Mol. Biol. 16:49, 1991); van der Zaal at al. (Plant Mol. Biol. 16:983, 1991).

Several reports have described sequences which direct expression of genes either predominantly in root tissues, or which express in various tissues including roots (Tingey et al., EMBO J. 6:1, 1987; An et al., Plant Physiol. 88:547, 1988; Oppenheimer et al., Gene 63:87, 1988; Conkling et al., Plant Physiol. 93:1203, 1990; Ohl et al., Cell 2:837, 1990; van der Zaal et al., Plant Mol. Biol. 16:983, 1991).

U.S. Pat. No. 4,803,165 (Applebaum) teaches the transformation of the nitrogen fixing organism, *Rhizobium japonicum*, to express the toxic crystal protein of *Bacillus thuringiensis* under control of the nif promoter of *R. japonicum*. U.S. Pat. No. 5,008,194 (Rolfe et al.) further teaches the transformation of *Bradyrhizobium japonicum*, to express the toxic crystal protein of *Bacillus thuringiensis* under control of the nifH promoter of *B. japonicum*. Because the transformed nitrogen fixing bacteria of Applebaum and Rolfe have symbiotic relationships that are confined in nature to the root nodules of the leguminous plants, Applebaum and Rolfe have no applicability to the non-leguminous plants of the world. Further, both Applebaum and Rolfe transform a symbiotic organism and not the plant itself. Accordingly, the seeds of the leguminous plants that were infected with the transformed organism are incapable of carrying the gene expressed by a bacterium in the root nodules of the parent plant. Thus, to utilize the inventions of Applebaum or Rolfe, purchasers of leguminous seed would also be required to purchase an appropriate transformed nitrogen fixing organism to infect their soils.

It is an object of the present invention to provide a means for conferring immunity or resistance to disease on any plant root that is susceptible to disease.

It is also an object of the present invention that the tract of immunity or resistance to a root disease be carried in the seeds of each succeeding generation of plant.

SUMMARY OF THE INVENTION

The present invention is directed to the components and methods for genetically transforming plants, particularly food crops, that have roots that are susceptible to fungal or insect diseases, whereupon the roots of the transformed plant express a toxin or substance that provides the immunity or resistance to fungal or insect disease.

The present invention has several aspects. In its first aspect, the present invention is directed to an isolated promoter element that exhibits root abundant expression. The isolated promoter element of the present invention comprises the nucleotide sequence of FIG. 7 (SEQ ID No. 5) and functionally equivalent nucleotide sequences that have at least 95% homology with the nucleotide sequence of FIG. 7 (SEQ. ID No. 5).

In another aspect, the present invention also encompasses a recombinant DNA molecule having the nucleotide sequence of FIG. 7 (SEQ ID No. 5) or that is functionally equivalent and 95% homologous to the sequence of FIG. 7 (SEQ ID No. 5).

The present invention is also directed to a recombinant DNA plasmid that is capable of functioning as a vector comprising the nucleotide sequence of FIG. 7 or a functionally equivalent nucleotide sequence having at least 95% homology to the nucleotide sequence of FIG. 7. Two examples of the plasmids of the present invention are pTZ11GUS and pALLTKRT1G.

The present invention further encompasses a method for conferring disease resistance or immunity on disease susceptible plant roots comprising the steps of:

a. isolating in any order, a promoter from a gene having root abundant expression, and a heterologous DNA fragment that encodes for a protein or peptide that is capable of conferring immunity or resistance to an insect and/or a fungal disease affecting a plant's roots;

b. inserting into a vector, individually or in combination, the isolated promoter and the heterologous DNA fragment from Step (a) such that said heterologous DNA fragment is both downstream from said promoter and so oriented relative to said promoter as to be under expressible control thereof;

c. transforming a disease susceptible species of plant, plant cell, or plant tissue protoplast, with said vector, whereupon the roots of the transformed plant express the protein or the peptide that confers upon said roots an immunity or a resistance to a disease that is not otherwise found in an untransformed plant of the same species.

BRIEF DESCRIPTION OF THE FIGURES

FIGS. 4-1 and 4-2. Complete nucleotide sequence (SEQ ID No. 1) of the genomic clone G11F, indicating the putative ATG translation start site (boxed) and stop site (dot underlined, the predicted transcription start site (arrow) based on the size of transcript and on the primer extension results, and the putative CAT and TATA regulatory sequences (solid underlined).

FIG. 6. Nucleotide sequence (SEQ ID No. 4) of the final "promoter" region obtained following PCR amplification. This fragment was digested with HindIII alone (since an error early in sequence determination resulted in failure to detect an internal XbaI site prior to synthesis of oligonucleotide primers), and the resulting fragment, having a HindIII-cut 5' end and a blunt 3' end, was cloned into the HindIII/SmaI-cut vector fragment of pALLTKRep to generate the vector shown in FIG. 8. FIG. 7. The 518 bp nucleotide sequence (SEQ ID No. 5) of the promoter in G11F. The promoter corresponds to the 518 base pairs that are immediately upstream from the ATG start site shown in FIG. 4.

DETAILED DESCRIPTION OF THE INVENTION

Figure 1:
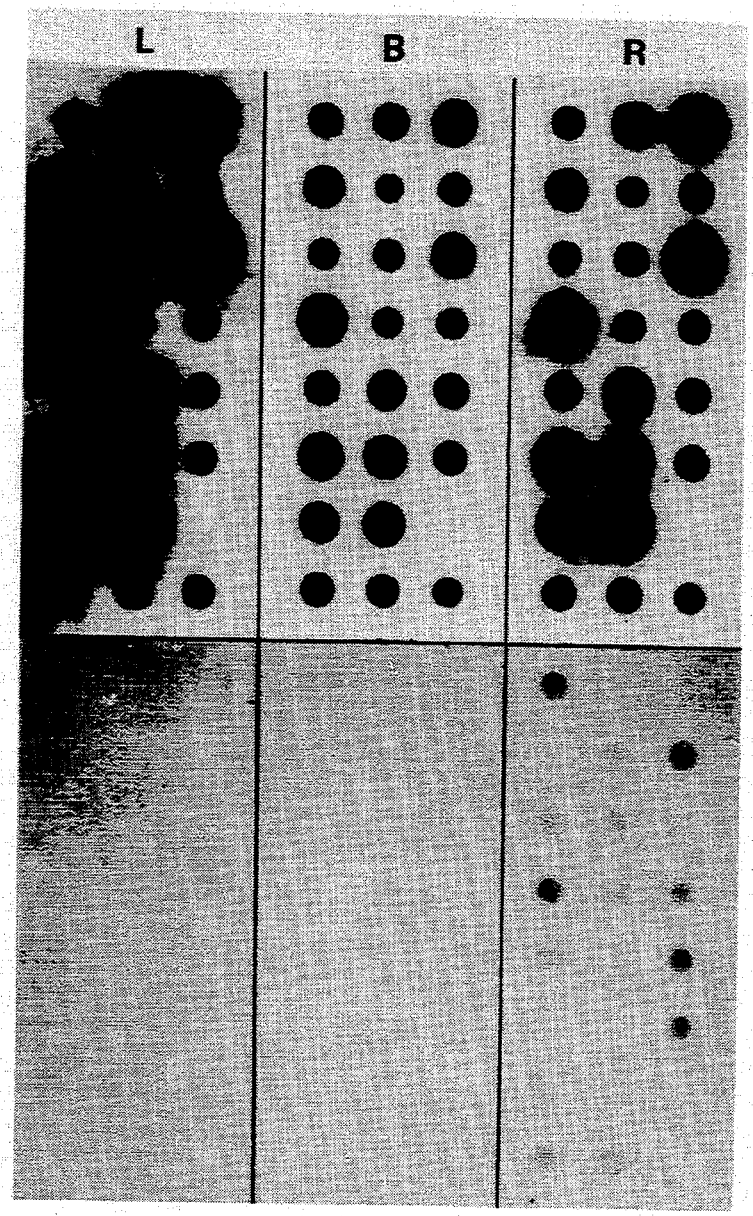
FIG. 1. Dot blot analysis of 22 isolates from a restreaked colony of the root cDNA clone, G1-3b, hybridized with single strand cDNA probes made from reverse transcription of leaf (L), flower bud (B) or root (R) poly(A)+ mRNA, and washed under low (2X SSC, 0.1% SDS, 40° C.) (top) and high (0.1X SSC, 0.1% SDS, 65° C.) (bottom) stringency, and subjected to autoradiography for 12 and 48 hours, respectively. The bottom right dot corresponds to pTZ18R vector, spotted as a control.

The present invention has multiple aspects. However, in its simplest form, it is directed to an isolated promoter having the nucleotide sequence of FIG. 7 (SEQ ID No. 5). The promoter of FIG. 7 was isolated from a structural gene having abundant expression in the roots of *Brassica napus* cd. cultivar Westar (Agriculture Canada, Saskatoon).

In the second aspect of the present invention, the isolated promoter element was ligated to a heterologous structural gene, the β-glucuronidase gene, to form a composite gene capable of demonstrating the functionality and specificity of expression of the promoter. This aspect of the present invention demonstrates the suitability of using this promoter in conjunction with a heterologous structural gene encoding a protein or peptide capable of conferring disease resistance or immunity to the roots of the plants that were susceptible to the disease By the word "disease" as used herein, is meant any adverse condition caused by an organism other than the plant itself which adversely affects either the growth rate or the vitality of the plant. The most common sources of disease to the roots of a plant are insects, insect larvae or fungi.

The word "plant" as used herein is meant to include any plant having a desirable property including aesthetic beauty or commercial value. Particularly preferred plants are those plants that provide commercially valuable crops, including food and tobacco.

In order for the isolated promoter element to control expression of a foreign structural gene, the foreign structural gene must lie "downstream" or alternatively on the 3' side of the promoter. Secondly, the distance in base pairs (bp') between the functional elements of the promoter, e.g., the transcription initiation site, and the translational ("ATG") start site also affect expression. Optimum distance can be achieved by experimentally varying the distance between the functional elements of the promoter and the ATG start site of the structural gene. As a general rule, reasonable operability is obtained when the distance between the promoter and the heterologous structural gene is similar to the distance between the promoter and the native gene that it normally controls. In the present invention, the isolated promoter of FIG. 7 incorporates all bases upstream of the ATG start site of its native gene. Accordingly, reasonable operability is expected with any heterologous gene that is capable of being ligated to the isolated promoter of the present invention.

To test the operability of the isolated promoter of the present invention, standard cloning techniques were used to ligate the promoter to the reporter gene already present in a binary vector, to form a composite gene in a vector suitable for transformation of tissue explants of *Brassica napus* by *Agrobacterium* co-cultivation. The resulting transformed canola plants were tested for expression of the reporter gene. The results indicate that the roots of *B. napus* successfully expressed the product of the heterologous reporter gene.

Construction and Screening of cDNA Library

Total RNA was extracted from 10 g of primary roots of 6–7 day old *Brassica napus* (cv. Westar) seedlings according to Cashmore (Meth. Chlor. Mol. Biol., Elsevier, Amsterdam, pp. 387–392, 1982). Poly(A)+ mRNA was purified by oligo (dT) cellulose chromatography and used to produce a directional plasmid-based cDNA library according to the method of Bellemare et al. (Gene 52:11-19, 1987).

The resulting cDNA library was plated out on 12 plates at a density of $2-4 \times 10^3$ cells per plate, and colony lifts were performed according to Sambrook et al. (A Laboratory Manual, Cold Spring Harbor Laboratory Press, 1982). Replicates of each plate were made to permit multiple probings. The filters were prehybridized for 2–6 hours at 42° C. in 50% formamide, 5X SSPE, 1% sodium dodecyl sulfate ("SDS"), 500 ug/ml heparin, 0.1% sodium pyrophosphate and 0.1 g/ml dextran sulfate. By "1X SSPE" is meant the following solution: 10 mM sodium phosphate, pH 7.4, 150 mM sodium chloride, 1 mM EDTA. Overnight hybridization of replicate blots was carried out in the same solution, containing as probe, single strand cDNA made from reverse transcription of poly(A)+ mRNA isolated previously from root, leaf, seed, or flower bud tissues. The blots were washed to high stringency (65° C. in 0.1X SSC, 1% SDS), wrapped in plastic wrap and subjected to autoradiography. By "1X SSC" is meant the following solution: 150 mM sodium chloride, 15 mM sodium citrate, pH 7.0. Colonies that produced positive hybridization signals on blots probed with root cDNA but not with cDNA probes for other tissues were transferred onto a master plate. Replicates were made and subjected to two more rounds of screening as above.

Putatively positive clones were selected. The positive clones were then replated to isolate new individual colonies and to ensure that more than one clone was not present in the original colony. The DNA from the isolated colonies was then subjected to dot blot analysis, using single strand cDNAs probes. The twenty-two (22) isolates from the one colony designated G1-3b which were analyzed by dot blots, yielded 13 clones which exhibited root-specific hybridization under high stringency washes (0.1X SSC, 0.1% SDS, 65° C.). Clone G1-3b #12 (hereinafter called G1-3b) was selected for further characterization. Restriction digests of DNA from this clone yielded an insert of only 311 nucleotides.

Figure 2:
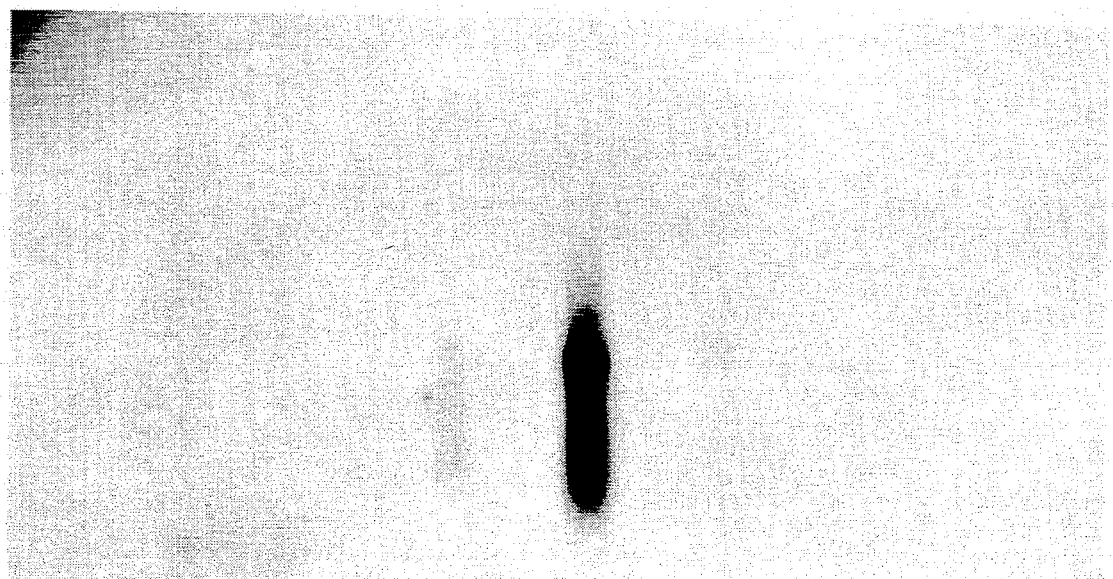
FIG. 2. Northern blot analysis of poly (A)+ mRNA from leaf (L, seed (S, flower bud (B, open flower (F, root (R, petal (P, anther (A) and stigma (T) tissues. The blot was probed with the PCR-amplified insert from the G1-3b cDNA clone, washed to high stringency (0.1X SSC, 0.5% SDS, 63° C.), and subjected to autoradiography for 3.5 days. Strong hybridization to a 1.2 kb band in root RNA is noted with faint hybridization to a similar size band in petal and anther tissues. No signal was observed in leaf, seed, flower, bud, or stigma tissues under these conditions.

To further establish the specificity of the G1-3b clone, a northern blot analysis was carried out. (FIG. 2). In the northern blot of FIG. 2, poly(A)+ mRNA (8–9 ug) from each of leaf, seed, flower bud, open flower, root, petal, anther and stigma tissues were separated on gels, and blotted. (Sambrook et al., A Laboratory Manual, Cold Spring Harbor Laboratory Press, 1982). Thereafter, the blot was probed with the PCR-amplified insert from the G1-3b cDNA clone and washed to high stringency (0.1X SSC, 0.5% SDS, 63° C.). The washed blot was subjected to autoradiography for 3.5 days. Strong hybridization to a 1.2 kb band in root RNA is noted with faint hybridization to a similar size band in petal and anther tissues. No signal was observed in leaf, seed, flower, bud or stigma tissues under these conditions.

Isolation and Characterization of Genomic Clones

The insert from cDNA clone G1-3b was excised and transferred into pDB21 (Boivin and Bellemare, GATA 8:181, 1991), a vector sharing no homology with pTZ18R (Mead et al, Prot. Engin. 1:67, 1986). The resultant plasmid was used to screen a pTZ18R-based genomic library constructed as 42 sub-fractions (Nantel et al., Plant Mol. Biol. 16:955, 1991). Two sub-fractions yielded positive hybridization signals using the G1-3b insert in pDB21 as a probe. These two subfractions were used for subsequent colony hybridization as described above. Two clones, designated G11F and G38F, from independent genomic subfractions were isolated and sequenced using the method of Sanger. (Sanger et al., Proc. Natl. Acad. Sci. USA 74:5463, 1977). The original G1-3b cDNA clone was also sequenced using the Sanger method.

The G1-3b insert in pDB21 was used to rescreen an independently constructed Brassica napus root cDNA library, yielding many homologous clones, which were subsequently sequenced and characterized (Bergeron et al., in preparation), and used to aid in identifying the 5', i.e., 5 prime regulatory sequences in the genomic clones.

Primer Extension

Two hundred ng of a synthetic oligonucleotide primer, PEG22 (5'-CCAACACCAACACCAG-CATCA), (SEQ ID No. 6) corresponding to a 21 bp sequence 155 nucleotides downstream of the predicted ATG start site were radiolabeled via an exchange reaction (Sambrook et al., A Laboratory Manual, Cold Spring Harbor Laboratory Press, 1982). Ten μg of total root RNA were denatured at 80° C. for 3 minutes in the presence of 80 ng of the labelled oligonucleotide primer. Reverse transcription buffer (final concentration 100 mM Tris-HCl pH 8.3, 2 mM $MgCl_2$ 50 mM KCl) was added and the mixture incubated for 45 minutes at 57° C. Thereafter, all four dNTPs (0.5 mM final each) and 200 U of RNAaseH$^-$ murine Moloney leukemia virus (M-MLV) reverse transcriptase (Bethesda Research Laboratories) were added to the mixture which was incubated for an additional 45 minutes at 50° C. RNA was degraded by a 30 minute incubation at 37° C. in the presence of 0.3M NaOH and the solution was neutralized with 0.1M Tris-HCl pH 7.5 and 0.3M HCl. Following phenol extraction, the nucleic acids were ethanol-precipitated. One half of the reaction mix was loaded and run on a 6% sequencing gel along with a sequence ladder of known size.

Identification And Isolation Of Root "Promoter"

Figure 3:
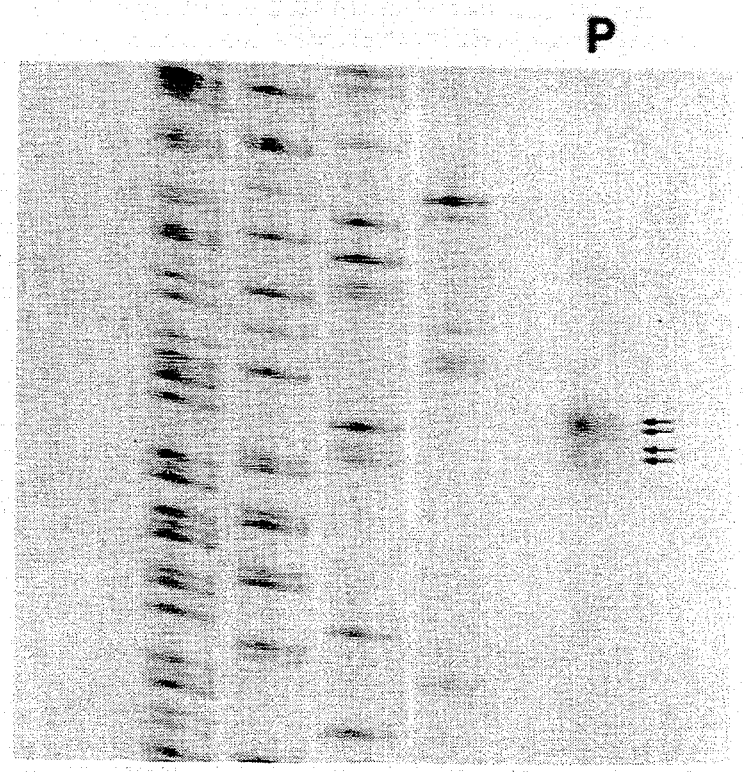
FIG. 3. Results from primer extension experiment using 10 ug of total *Brassica napus* root RNA as template and oligonucleotide PEG22, as primer as outlined in the text. To determine the sizes of the primer extension products (P), a sequencing reaction was run on a DNA sample of known sequence and loaded on the sequencing gel in adjacent wells. Four bands (arrows) with sizes of 35, 36, 38 and 39 nucleotides (bottom to top) were obtained.

Of the several G1-3b-related cDNA clones recovered from screening the new root cDNA library, none appeared to be full length based on the predicted transcript size of 1.2 kb. From the sequence of the genomic clone G11F (FIG. 4), a putative ATG translation start site was identified. The identification of the start site was based on the size of the transcript, on the assumption of no introns, and also on the presence of CAT-and TATA-like sequences a short distance upstream of this ATG. To verify the position of the ATG start site, primer extension was carried out, using total RNA and a labelled oligonucleotide that hybridized to a sequence 155 nucleotides downstream of the putative ATG. Four sharp, equally intense bands (39, 38, 36 and 35 nucleotides 5' to the putative ATG) were observed on the autoradiograph (FIG. 3). We attribute the presence of more than one band to the presence of multiple homologous transcripts (this root clone is part of a gene family) which may differ slightly in length of transcript leader sequences, or alternatively to premature stops of the reverse transcriptase enzyme. The size of the primer extension products obtained, however, confirmed that the predicted translational start site in G11F was in fact the real start site as indicated on the nucleotide sequence of FIG. 4.

Figure 5:
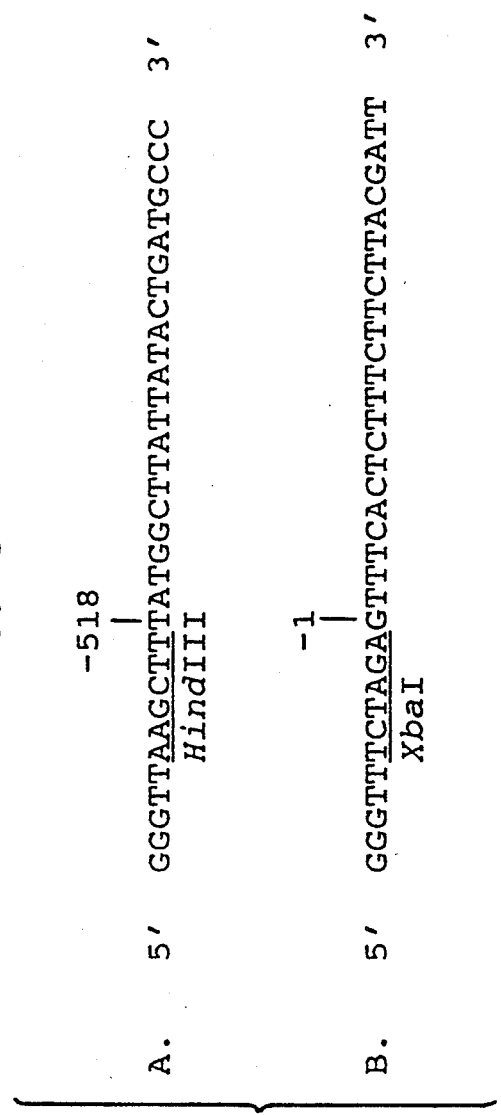
FIGS. 5A and 5B. Synthetic oligonucleotides A and B used for PCR amplification of the upstream region of G11F. Oligonucleotide A (SEQ ID No. 2 ), starting with the sequence 5'TATGGCT . . . 3', corresponds in part to nucleotides −518 to a −496 on the sense strand, while oligonucleotide B (SEQ ID No. 3 ), starting with 5'GTTTCAC . . . 3', corresponds in part to nucleotides −1 to −24 on the antisense strand of the promoter region. The additional nucleotides on the 5' end of each oligonucleotide provide restriction sites ( as indicated) for cloning, in addition to the option for cloning using blunt ended DNA fragments.

Based on the available sequence 5' to the ATG start site, two complementary oligonucleotides, Oligonucleotides A and B respectively, were synthesized, and used for PCR amplification of the upstream region of G11F. The first oligonucleotide, Oligonucleotide A (SEQ ID No. 2), is a 34 bp synthetic oligonucleotide. The 3' end of Oligonucleotide A, starting with the sequence 5'ATGGCT . . . 3', corresponds to nucleotides −518 to −496 on the sense strand. As shown in FIG. 5, Oligonucleotide A also incorporates the HindIII restriction site AAGCTT at a position immediately upstream to the nucleotide corresponding to base pair −518 on the sense strand.

Oligonucleotide B (SEQ ID No. 3) is a 35 bp synthetic oligonucleotide. The 3' end of Oligonucleotide B, starting with 5'GTTTCAC . . . 3', corresponds to nucleotides −1 to −24 on the antisense strand of the promoter region. As shown in FIG. 5, Oligonucleotide B also incorporates the six nucleotides TCTAGA that correspond to the XbaI restriction site. The resulting promoter with both the HindIII and XbaI restriction sites at its 5' and 3' ends respectively is shown in FIG. 6 (SEQ ID No. 4). The XbaI restriction site allows the addition of any foreign structural gene or any foreign DNA fragment downstream from the promoter fragment. Although only the HindIII and XbaI restriction sites are mentioned above, those of ordinary skill in the art would recognize that other restriction sites would work equally as well. The following publications, which are hereby incorporated by reference, list numerous restriction sites that are available to those of ordinary skill in the art: Maniatis, T., et al. (1982) "*Molecular Cloning: A Laboratory Manual*" Cold Spring Harbor Laboratory, New York, pp. 98–106; and Bellemare, G. and Potvin, C. (1990), "Classification of Type-II Restriction Endonucleases and Cloning of Non-identical Cohesive-end Fragments Without Self-polymerization Using Nonpalindromic Oligodeoxyribonucleotide Adapters," Gene 101: 67–74.

Given the teaching of the nucleotide sequence of the 518bp promoter of the present invention, (FIG. 7; SEQ ID No. 5) and the bases in various restriction sites, one of ordinary skill could clone the promoter of the present invention (SEQ ID No. 5) with a variety of compatible restriction sites at its 5' and 3' ends. Thus, in its simplest aspect, the present invention encompasses an isolated promoter element comprising the nucleotide sequence of FIG. 7 (SEQ ID No. 5).

Those of ordinary skill in the art would recognize that not every bp of a promoter element is essential for retention of promoter activity. The removal of or the substitution of a non-effective amount of base pairs would not result in the loss of promoter activity. The present inventors have no reason to assume that the loss of 5% homology with the sequence of FIG. 7 (SEQ ID No. 5) would adversely affect promoter activity. Accordingly, an isolated promoter having at least 95% homology with the promoter sequence of FIG. 7 (SEQ ID No. 5) and being functionally equivalent thereto is also within the scope of the present invention.

Finally, the present invention encompasses a recombinant DNA molecule comprising a promoter of a gene exhibiting root abundant expression in Brassica sp. and comprising the sequence of FIG. 7 (SEQ ID No. 5).

Composite Genes

In another aspect, the present invention is also directed to a composite gene comprising a promoter having the nucleotide sequence of FIG. 7 (SEQ ID No. 5) and a heterologous structural gene, under control of said promoter, preferably a structural gene capable of conferring disease resistance or immunity to the roots of a disease susceptible plant.

The choice of structural gene that is under control of the root promoter of the present invention will depend upon the disease or diseases to which the plant root is susceptible. For example, if the plant root is susceptible to consumption by lepidopteran larvae, the crystal protein of *Bacillus thuringiensis*, which is also known as the delta-endotoxin, has been reported to be effective. See Wong et al., J. Biol. Chem, 258; 1960 (1983). Wong et al, which is incorporated herein by reference, discloses the DNA sequence for 999 bp of the crystal protein sequence and the 5' flanking sequence of 176 bp. U.S. Pat. No. 4,803,165, which teaches the isolation of the crystal protein gene of *B. thuringiensis* from pESI (ATCC No. 31995), is incorporated herein by reference. Also incorporated herein by reference is U.S. Pat. No. 5,073,632 which teaches a purified and isolated gene having the nucleotide sequence coding for the amino acid sequence for the CryIIB crystal protein from *Bacillus thuringiensis*; and U.S. Pat. No. 5,080,897 which teaches novel *Bacillus thuringiensis* strains and related insecticidal compositions.

A composite gene of the present invention having both the promoter of the present invention and the crystal protein gene under its control is made by cloning the crystal protein gene using the techniques described above for cloning the promoter of FIG. 6 (SEQ ID No. 4). By selecting the same restriction sites at the 3' end of the promoter and at the 5' end of the crystal protein gene, with the proviso that they are unique to both nucleic acid segments, the 3' end of the promoter and the 5' end of the crystal protein gene are capable of being ligated after digestion with the appropriate restriction endonuclease. In the resultant composite gene, the expression of the crystal protein is under control of the promoter of FIG. 7. By varying the distance between the promoter and the crystal protein gene, one of ordinary skill in the art could optimize the expression of the crystal protein. The distance may be varied by using conventional cloning techniques such as by cloning a promoter having either additional or fewer base pairs at its 3' end. The lengthened or shortened promoter is then ligated to an appropriate restriction site at the 5' end of the structural gene. Alternatively, the distance between the promoter and the structural gene may be lengthened by cloning additional bases upstream of the ATG start site but downstream from the restriction site that is used to ligate the gene to 3' end of the promoter. Other modifications, such as base changes to optimize codon usage or addition of enhancer sequence(s), can further improve expression of the structural gene.

The above description teaches a composite gene having the complete crystal protein gene under control of the promoter of the present invention. However, in certain situations, it may be advantageous to substitute a partial protein gene, such a gene that encodes for an insecticidally toxic fragment of the crystal protein. The term "insecticidally toxic fragment," as used herein, is meant to encompass those fragments, whether protein or polypeptide, that are either toxic or that are capable of being rendered toxic by one or more enzymes in the insect's gut. Such partial protein genes for the crystal protein of *B. thuringiensis* are disclosed by Schnepf et al., J. Biol. Chem., 260:6273-80 1985, which is incorporated herein by reference. Both the construction of partial genes and testing for the retention of toxicity are techniques that are well known to the art.

The present invention also addresses a second major cause of root disease in plants—fungi. Where a plant's roots are susceptible to a fungal disease, the structural gene that is under control of the isolated promoter of the present invention would encode for a fungistatic or a fungicidal agent. By fungistatic or fungicidal agent is meant a chemical substance, typically a protein or a peptide, that inhibits a fungus or that destroys a fungus respectively.

Vector Construction

Figure 8:
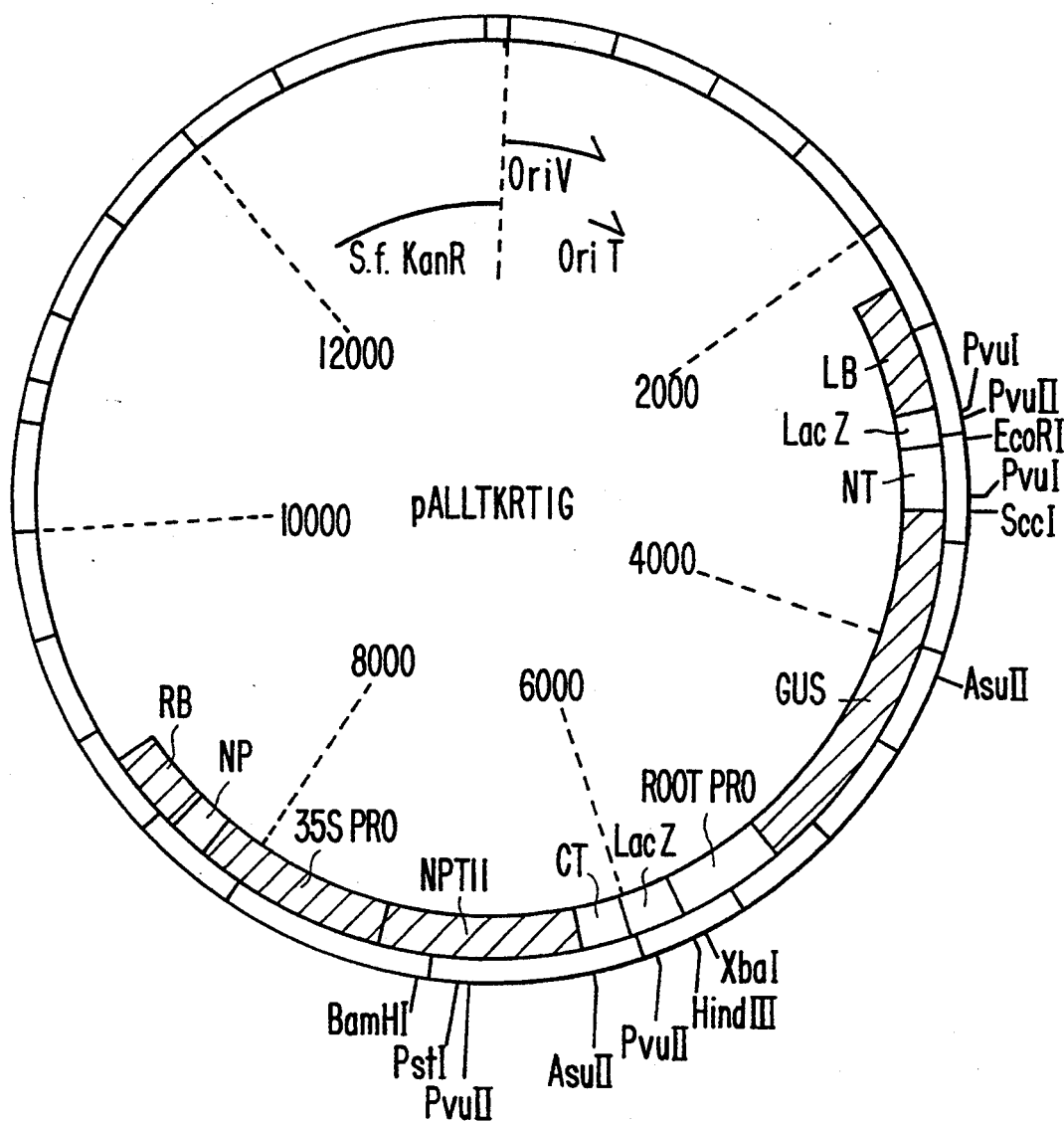
FIG. 8. Map of the binary vector pALLTKRT1G in which the root promoter was cloned in front of the GUS reporter gene in binary vector pALLTKRep.

In another aspect, the present invention is directed to a recombinant DNA plasmid which is capable of functioning as a vector, comprising the nucleotide sequence of FIG. 7 (SEQ ID No. 5). By way of example, the promoter region corresponding to FIG. 6 (SEQ ID No. 4) was purified and used in construction of the binary plant transformation vector pALLTKRT1G. As shown in FIG. 8, the promoter having at the 5' end, a HindIII restriction site, and at the 3' end, a blunt end corresponding to the natural 3' end of the PCR amplified "promoter" region, was cloned upstream of a gene encoding β-glucuronidase ("the GUS reporter gene") in the binary vector pALLTKRep, using the unique HindIII and SmaI sites of pALLTKRep. For construction of the vector pALLTKRep, the NheI/ClaI vector component of pBI101.3 (from Clonetech, Palo Alto, Calif.) and the XbaI/SmaI insert component of pALLNPT1 (a vector essentially equivalent to pALL-Kanl, the construction of which was described in Arnoldo et al., 1991) were purified, and overhanging ends were 'filled in' by incubation at room temperature for 25 minutes in the presence of the four dNTPs and DNA polymerase I (Klenow fragment), followed by overnight ligation at 15° C. in the presence of T4 DNA ligase. Arnoldo, et al., (1992) "Evaluation of Transgenic Plants Under Field Conditions," Genome 35: 58–63. Clones containing correctly oriented inserts were selected by analyzing DNA with restriction enzymes.

Figure 9:
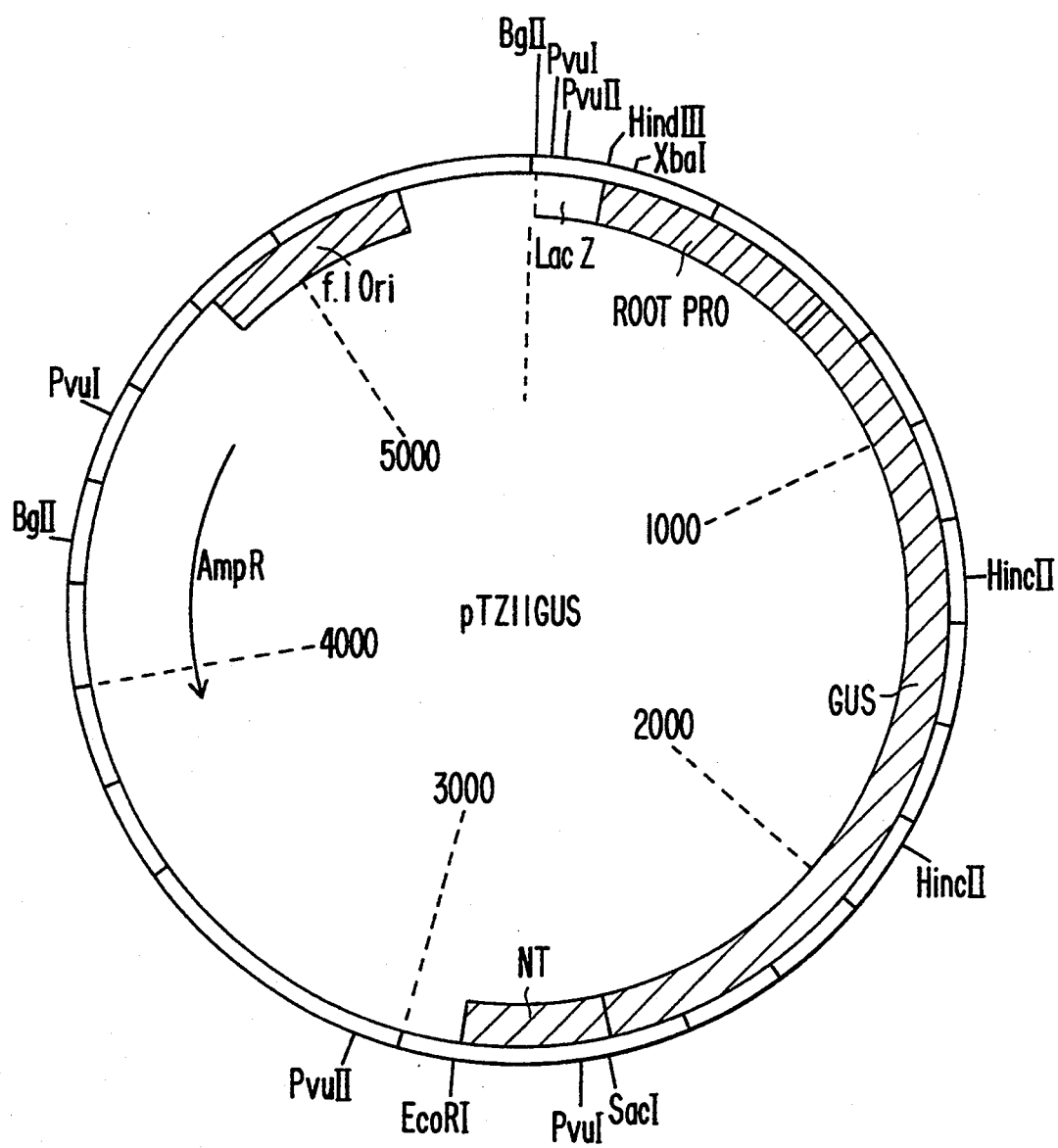
FIG. 9. Map of vector pTZ11GUS in which the 2.7 kb EcoRI/HindIII fragment that contained the root-promoter-GUS gene cassette of pALLTKRT1G was transferred into the EcoRI/HindIII cut pTZ18R vector.

A second vector, pTZ11GUS (FIG. 9), was also constructed by removing the 2.7 kb EcoRI/HindIII fragment containing the root promoter-GUS gene cassette of pALLTKR1G and inserting it into the EcoRI/HindIII cut pTZ18 vector. The pTZ18 vector is available from Pharmacia P-L Biochemicals, Inc. (Milwaukee, Wis.). The pTZ11GUS construct was then used for sequencing the promoter-gene junction to verify the absence of any mutations that may have arisen during PCR amplification or cloning. No differences from the corresponding sequence of the genomic clone were found.

Plant Transformation

The present invention also encompasses a method for conferring disease resistance or immunity upon plant roots that are susceptible to a disease comprising the steps of:

a. isolating in any order, a promoter from a gene having root abundant expression, and a heterologous DNA fragment that encodes for a protein or peptide that is capable of conferring immunity or resistance to an insect or a fungal disease affecting a plant's roots;

b. inserting into a vector, individually or in combination, the isolated promoter and the heterologous DNA fragment from Step (a) such that said heterologous DNA fragment is both downstream from said promoter and so oriented relative to said promoter as to be under expressible control thereof;

c. transforming a disease susceptible species of plant, plant cell, or plant tissue protoplast, with said vector, whereupon the roots of the transformed plant express the protein or the peptide that confers upon said roots an immunity or a resistance to a disease that is not otherwise found in an untransformed plant of the same species.

In the present invention, the seeds of the transformed plant carry the gene that confers immunity or resistance to a root disease.

The method of transforming a plant according to the present invention is often dependent upon whether the disease susceptible plant to be transformed is classified as monocotyledonous (a monocot) or as dicotyledonous (a dicot). A plant is a monocot if its sprouting seed has a single leaf. By way of example, monocots include corn, wheat, rye, oats, barley, sorghum, rice, grasses, and the like. A plant is dicot if its sprouting seed has two leaves. The dicotyledonous plants include fruiting trees, vines, and shrubs, and most vegetables and flowers. The mechanisms for transformation of a monocot and a dicot differ from one another.

Most of the dicotyledonous plants, and a few monocots, (lily and asparagus) are susceptible to crown gall disease in which tumors, reflecting uncontrolled cell growth, appear at the site of a wound. The tumors are caused by infection with the soil borne bacterium *Agrobacterium tumefaciens*. Dicots that are susceptible to crown gall disease are capable of transformation using *A. tumefaciens* that is carrying an intact Ti (tumor inducing) plasmid.

Transforming a susceptible dicot is begun by first inserting the gene to be expressed, such as the composite gene of the present invention, into a non-essential region of the T-DNA of a Ti plasmid or into a plasmid, such as pBR322, into which the T-DNA has been inserted. The techniques for such gene insertion are well known in the art as reflected in the following disclosures which are incorporated herein by reference. Schell et al., 1983 "The Ti Plasmids as Natural and Practical Gene Vectors for Plants," Biotechnology 1:175–180; Herrera—Estrella et al., 1984 "Light-Inducible and Chloroplast-Associated Expression of a Chimeric Gene Introduced Into *Nicotiana Tobacum* Using a Ti Plasmid Vector," Nature 310: 115–120; Peralta et al., 1985 "T-DNA Border Sequences Required For Crown Gall Tumorigenesis," Proc. Natl Acad Sci 82; 5112–5116; and Barton et al., 1983 "Regeneration of Intact Tobacco Plants Containing Full Length Copies of Genetically Engineered T-DNA, and the Transmission of T-DNA to R1 Progeny," Cell 32: 1033 –1043.

The plasmid containing the composite gene of the present invention in a non-essential region of the T-DNA is then introduced into the bacterium *A. tumefaciens* that is carrying an intact Ti plasmid. Upon infection of a plant at a wound site with these bacteria, the gene products of the vir region on the intact Ti plasmid mobilize the recombinant T-DNA which then integrates into the plant genome. The resulting transformed plant cells or parts are regenerated into transformed plants using plant regeneration techniques that are well known to those of ordinary skill in the art. See for example, Ellis et al., "Tissue specific expression of pea legumin gene in seeds of *Nicotiana plumbaginifolia*," Plant Mol. Biol. 10: 203–214 (1988) which is incorporated herein by reference. Plants that are regenerated by this technique carry the composite gene of the present invention in both their somatic cells and in their germ cells. Accordingly, a plant transformed according to the present invention is not only capable of expressing a heterologous structural gene under control of the promoter of FIG. 7 (SEQ ID No. 5), but it is also capable of passing that trait on to its progeny.

Figure 12A:
FIGS. 12A–12H. Histochemical GUS assay results demonstrating positive GUS expression (dark or black sections) in roots and root hairs of R1 seedlings derived from transgenic canola plants transformed with the pALLTKRT1G vector (A-D) or with a vector containing the GUS gene behind a CaMV 35S promoter (E, positive control), while no activity is detected in roots of the untransformed *B. napus* plant (F, negative control) or in leaf (G) or petiole (H) tissues of the pALLTKRT1G transgenics.
Figure 12B:
Figure 12C:
Figure 12D:
Figure 12E:
Figure 12F:
Figure 12G:
Figure 12H:

To test the capability of the promoter to express the GUS reporter gene, the pALLTKRT1G vector was introduced into Brassica napus via *Agrobacterium* co-cultivation of cotyledon explants essentially as described in Moloney et al., Plant Cell Rep. 8:238–242 (1989). Selfed seeds from regenerated plants were collected and germinated for 7–20 days on GM medium (MS organics, 3% sucrose, 0.2% Gel-rite). Clones of the plantlets were maintained in culture, and one set of clones was transferred to soil in a greenhouse for recovering mature transgenic plants and seed for R2 population analysis. Excised roots from kanamycin resistant seedlings in culture were assayed for β-glucuronidase activity by incubation in 100 mM sodium phosphate buffer, pH 7.0, containing 0.5 mM $K_3[Fe(CN)_6]$, 0.5 mM $K_4[Fe(CN)_5]$, 1 mM EDTA and 2 mM X-Gluc. ("X-Gluc" is 5-bromo-4-chloro-3-indoyl-beta-glucuronide, which is commercially available, such as from Clontech Laboratories, Inc., Palo Alto, Calif.). GUS activity was detected as patches of blue staining at the junction of primary and lateral roots and as streaks in the lateral roots; root hairs also stained blue (FIG. 12A–D). While seedlings transformed with a vector containing the GUS gene driven by a CaMV 35S promoter yielded blue staining roots (positive control, FIG. 12E), GUS activity was not detectable in: i) roots from non-transformed seedlings (FIG. 12F); or ii) leaf or petiole tissues from the seedlings derived from pALLTKRT1G-transformed plants (FIG. 12G–H). This establishes the root-specificity of this promoter.

The binary vector pALLTKRT1G is primarily useful for the transformation of dicots, via an *Agrobacterium* system as described above, but this vector as well as non-binary derivatives can also be useful in direct DNA transformation methods, such as particle bombardment (Wang et al., Plant Mol. Biol. 11:433–439, 1988; Chibbar et al., Genome 34:453–460, 1991), electroporation (Fromm et al., Proc. Natl. Acad. Sci. USA 82:5824–5828, 1985; Rhodes et al., Science 240:204–207, 1988), or other non-*Agrobacterium*-based systems (Cutler et al. J. Plant Physiol. 117;29–40, 1984; Reich et al., Bio/Technology 4:1001–1004, 1986; de la Pena et al., Nature 325:274–276, 1987), all of which are incorporated herein by reference.

As mentioned above, only two monocots (lily and asparagus) are capable of infection and transformation by *A. tumefaciens*. Accordingly, different techniques, such as the direct DNA transformation methods mentioned above, are required to transform economically important monocots, such as corn, wheat, rye, rice, barley, oats, sorghum and the like.

Figure 10:
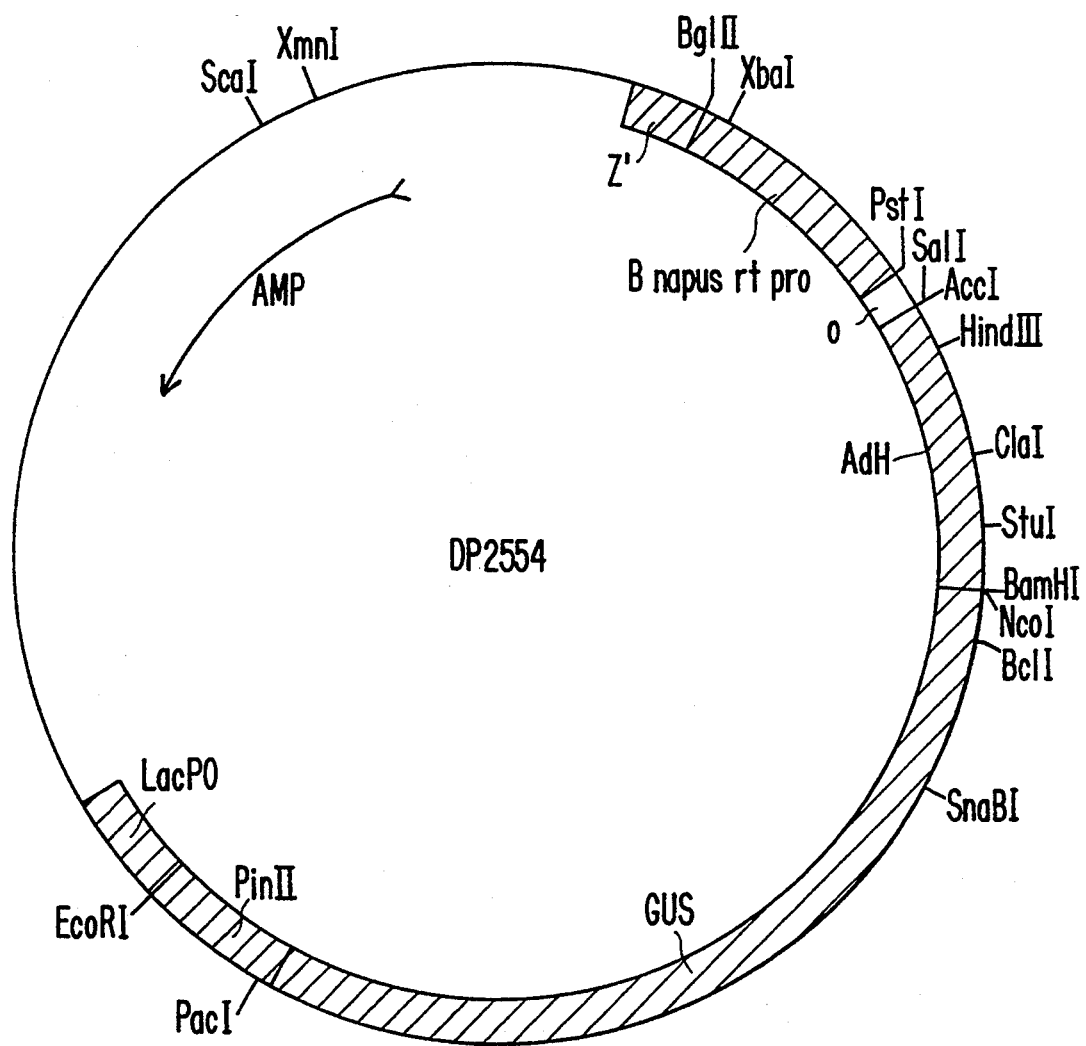
FIG. 10. Map of vector DP2554 in which the PCR-amplified root promoter was cloned in front of a reporter gene cassette, which included a tobacco mosaic virus omega prime (O') leader sequence, a corn alcohol dehydrogenase intron sequence (AdH), the GUS gene and a potato proteinase inhibitor gene terminator (PinII). This reporter cassette was previously found to express well in corn.

To test the utility of the promoter of the present invention for tissue specific gene expression in monocots, two additional vectors were constructed. The first vector is DP 2554 (FIG. 10). As shown in the map of FIG. 10, DP 2554 contains the PCR-amplified root promoter of the present invention (B. napus rt pro) in front of a reporter gene cassette which included a tobacco mosaic virus omega prime (O') leader sequence, a corn alcohol dehydrogenase intron sequence (AdH), the GUS gene, and a potato proteinase inhibitor gene terminator (PinII). This reporter cassette was previously found to express well in corn and monocots in general and is more fully discussed in copending U.S. Ser. No. 07/387,739 which is incorporated herein by reference.

Figure 11:
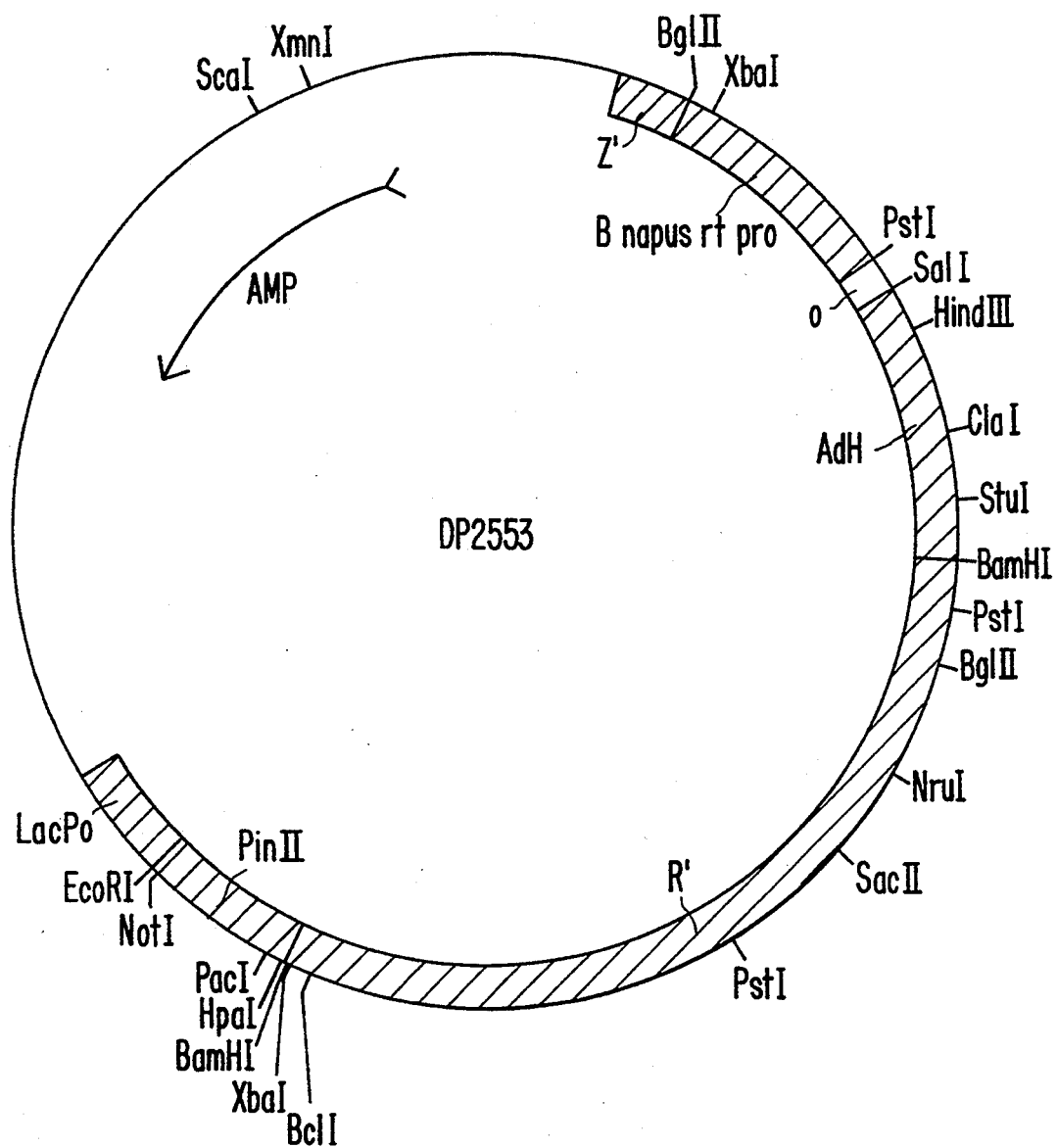
FIG. 11. Map of vector DP2553 which is structurally similar to DP2554 (FIG. 10) except for containing the corn R' gene as the reporter gene. This reporter cassette was also previously found to express well in corn.

The second vector is DP2553 (FIG. 11). As shown in its map at FIG. 11, DP2553 is structurally similar to DP2554 except that its reporter cassette contains the corn R' gene instead of the GUS gene. This reporter cassette is also discussed in our copending application U.S. Ser. No. 07/387,739. It is believed the components of these reporter cassettes could also work in monocots although probably with less efficiency. The recited combinations of components simply maximize the likelihood of detecting reporter gene expression from an introduced promoter even if it were a weak promoter.

In addition to the techniques described above, a susceptible plant could be transformed to express a composite gene of the present invention by other transformation techniques that are known to the art for the introduction of vectors into plants or plant cells which include but are not limited to calcium phosphate coprecipitation techniques, liposomes, protoplast fusion, micro- or macro-injection, and infection with viruses.

---

We claim

1. An isolated polynucleotide having the sequence of FIG. 7 (SEQ ID No. 5).

2. A recombinant DNA molecule comprising an isolated polynucleotide having the nucleotide sequence of FIG. 7 (SEQ ID No. 5).

3. A recombinant DNA plasmid comprising an isolated polynucleotide having the nucleotide sequence of FIG. 7 (SEQ ID No. 5).

4. The recombinant DNA plasmid of claim 3, comprising a plasmid selected from the group consisting of pTZ18R and PALLTKREP.

5. The recombinant DNA plasmid of claim 3 comprising pZ11GUS.

6. The recombinant DNA plasmid of claim 3 comprising pALLTKRT1G.

7. A recombinant DNA expression construct for use in constructing a *Brassica* strain that produces a heterologous protein in its roots, said construct comprising DNA coding for said heterologous protein linked operably with a promoter enabling constitutive expression thereof, said constitutive promoter comprising the nucleotide sequence of FIG. 7 (SEQ ID No. 5).

8. A composite gene for use in the root specific expression of a heterologous structural protein comprising a promoter, having the nucleotide sequence of FIG. 7 (SEQ ID No. 5), operably linked to a heterologous structural gene that encodes for said heterologous structural protein.

9. The isolated polynucleotide of claim 1, said polynucleotide being capable of promoting the downstream expression of heterologous structural gene that is operably linked thereto.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:1:

AGCTTAAAAA GAAAGAAAA AAAGAAAAAA GAAAGAA     37

( 2 ) INFORMATION FOR SEQ ID NO:2:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:2:

AGCTTTCTTT CTTTTTTCTT TTTTTCTTTT CTTTTA     37

( 2 ) INFORMATION FOR SEQ ID NO:3:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: Other Nucleic Acid ( i i i ) HYPOTHETICAL: YES ( i v ) ANTI-SENSE: NO ( x i ) SEQUENCE DESCRIPTION: SEQ ID NO:3:

CACACTTTTT CTTTCTTTT TTTCACACTT TTTTTCTTTT CTTTTT     46

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other Nucleic Acid (iii) HYPOTHETICAL: YES (iv) ANTI-SENSE: NO (xi) SEQUENCE DESCRIPTION: SEQ ID NO:4:

CANGACGTTG TAAAACGACG GCCAGT      26